United States Patent [19]
Georgette

[11] Patent Number: 5,201,766
[45] Date of Patent: Apr. 13, 1993

[54] PROSTHETIC DEVICE WITH POROUS MATRIX AND METHOD OF MANUFACTURE

[75] Inventor: Frederick S. Georgette, Memphis, Tenn.

[73] Assignee: Smith & Nephew Richards Inc., Memphis, Tenn.

[21] Appl. No.: 663,291

[22] Filed: Feb. 28, 1991

Related U.S. Application Data

[63] Continuation of Ser. No. 291,532, Dec. 29, 1988, abandoned, which is a continuation of Ser. No. 65,179, May 29, 1987, abandoned, which is a continuation of Ser. No. 774,957, Sep. 11, 1985, abandoned.

[51] Int. Cl.$^5$ .......................... A61F 2/28; A61F 2/54
[52] U.S. Cl. ........................................ 623/16; 623/18; 623/21; 623/22; 623/66
[58] Field of Search ............................... 623/16, 18

[56] References Cited

U.S. PATENT DOCUMENTS

| | | | |
|---|---|---|---|
| 3,855,638 | 12/1974 | Pilliar | 623/16 |
| 3,939,241 | 2/1976 | Powell et al. | 264/338 X |
| 4,021,910 | 5/1977 | Freeman, Jr. et al. | 29/526.2 |
| 4,041,123 | 8/1977 | Lange et al. | 264/338 X |
| 4,156,943 | 6/1979 | Collier | 623/23 |
| 4,374,669 | 2/1983 | MacGregor | 427/2 X |
| 4,550,448 | 11/1985 | Kenna | 623/16 |
| 4,612,160 | 9/1986 | Donlevy et al. | 419/2 |
| 4,644,942 | 2/1987 | Sump | 623/16 |
| 5,030,233 | 7/1991 | Ducheyne | 623/66 X |
| 5,057,101 | 10/1991 | Dorr et al. | 623/18 X |

Primary Examiner—David Isabella
Assistant Examiner—Dinh X. Nguyen
Attorney, Agent, or Firm—Pravel, Gambrell, Hewitt, Kimball & Krieger

[57] ABSTRACT

A method of forming a porous matrix and a porous matrix having a uniform surface, depth and a controlled microstructure is provided. The uniform matrix to provide for fixation of prosthetic device by tissue ingrowth is formed through the action of heat and pressure in a hot isostatic pressing process. Such a process provides a porous matrix having a uniform surface and depth due to the isostatic pressure applied and a controlled microstructure of the material due to the relatively low temperatures employed.

15 Claims, 3 Drawing Sheets

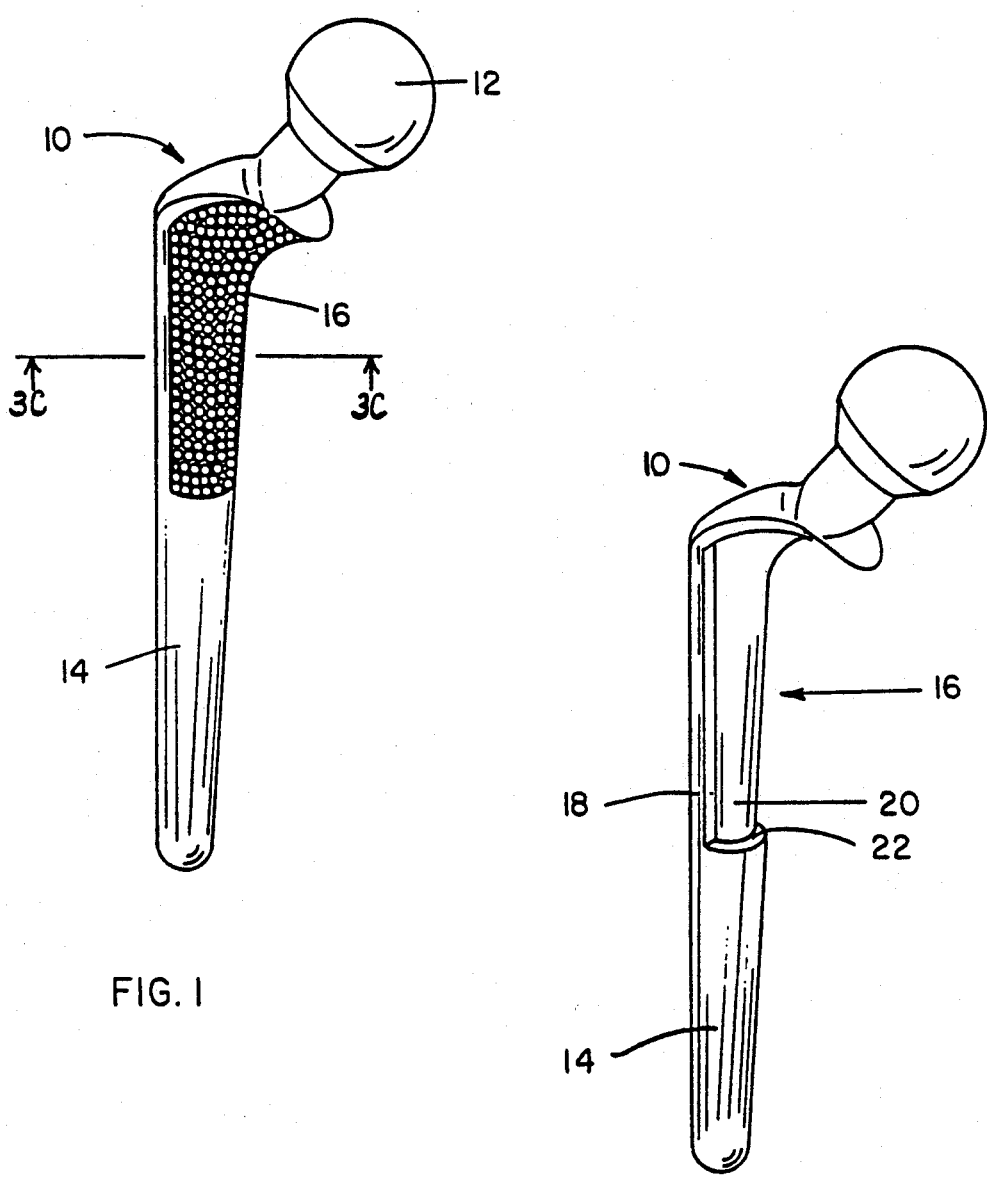
FIG. 1
FIG. 2
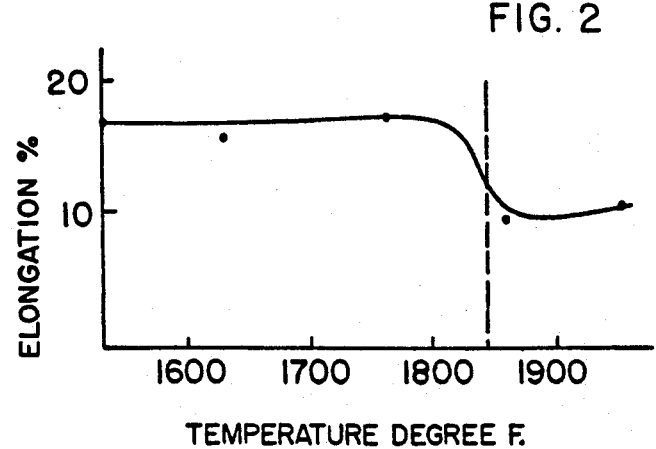
FIG. 5

PROSTHETIC DEVICE WITH POROUS MATRIX AND METHOD OF MANUFACTURE

This is a continuation of co-pending application Ser. No. 07/291,532 filed on Dec. 29, 1988, now abandoned, which is a continuation of Ser. No. 07/065,179 filed on May 29, 1987, now abandoned, which is a continuation of Ser. No. 06/774,957 filed on Sep. 11, 1985, now abandoned.

FIELD OF THE INVENTION

The present invention relates to a prosthetic device with a porous matrix on its outer surface that accommodates tissue ingrowth for anchoring the device in place.

BACKGROUND OF THE INVENTION

Prosthetic devices for the partial or total replacement of hips, knees and other parts of the human body are widely used. These implant devices are typically formed of materials such as stainless steel, cobalt-chromium-molybdenum alloys and titanium alloys since those materials are biocompatible and exhibit relatively low corrosion rates in body fluids.

For many years, implants were anchored in place through pressure or frictional fit, screws or glue-like materials such as polymethyl methacralate (PMMA). Because of various inadequacies in these fixation techniques, implants were developed that could take advantage of a phenomenon known as tissue ingrowth where bone or soft body tissue would grow into a porous matrix formed on the outer surface of the implant and firmly anchor it in place. Porous surfaces formed of various ceramic, metallic and polymeric materials have been developed.

The advantages of providing an area receptive to tissue ingrowth include providing an implant with a greater interface shear strength between the implant and the bone as well as a more uniform distribution of stresses throughout the implant and surrounding tissue. The goal in the use of such implant devices is to provide for fixation approaching the strength and resilience of natural bone and other tissue.

An example of an early attempt to develop a prosthesis capable of accommodating tissue ingrowth is described in U.S. Pat. No. 3,605,123 where an implant was described as being formed with a cast or wrought substrate and a porous metal overlay. The overlay or coating was applied by a plasma flame spray process, which resulted in a coating with a graduated or uneven porosity from the substrate to the surface. Aside from inadequacies in the use of plasma spray techniques in the formation of porous coatings, a non-uniform porous matrix has been found not to be effective in accommodating tissue ingrowth throughout the matrix resulting in a weaker bond than desired between the implant and surrounding tissue.

Much effort has been directed toward developing an implant with a porous matrix where the pores are substantially uniformly distributed throughout the matrix. One such attempt is described in U.S. Pat. No. 4,206,516 where titanium particles were bonded to a substrate through a sintering process, resulting in a porous coating with an irregular surface, but which had a relatively uniform pore distribution throughout.

A drawback of forming a porous matrix of materials such as titanium as described in U.S. Pat. No. 4,206,516 is that a sintering process normally requires elevated temperatures. For titanium, the microstructure of the naturally occurring mix of fine grained alpha and beta phases is transformed to a pure beta structure when heated to a temperature above about 990° C. (well below the temperature required for sintering), however, upon cooling the beta grains lose their identity (even though their outline remains) and the phases become redistributed such that the desirable physical properties of the metal are lost. Some of these possible recombinations include coarse grained alpha-beta phases and a mix of primary alpha and transformed beta phases. See L. J. Bartlo, *Effect of Microstructure on Fatigue Properties of Ti-6Al-4V Bar*, American Society for Testing and Materials, 1960, pp. 144–154.

Titanium that has been transformed into and out of the pure beta structure is significantly less desirable than the naturally occurring structure because of a decrease in fatigue strength and ductility. The normal sintering, although capable of providing uniformly distributed pores throughout a matrix, does not result in a pore size range that is controlled closely enough.

U.S. Pat. No. 3,852,045 teaches a porous material and method of production in which an attempt is made to provide better control over the pattern of interconnected pores or voids. The method involves a high energy rate forming process that compacts a metallic powder placed around a former through extremely high pressures created through high energy rate compaction. The compacted element is subjected to a high temperature, vacuum treatment to remove the former and to sinter the material. However, this process also employs sintering temperatures above the level that affects the microstructure of materials such as titanium.

SUMMARY OF THE INVENTION

The present invention relates to a porous matrix useful for prosthetic devices, which has a controlled surface configuration, depth and microstructure that is uniform from implant to implant, and a method of forming such a porous matrix.

The porous matrix is formed under pressure by a hot isostatic pressing process similar to that described in U.S. Pat. No. 4,041,123, which does not require a temperature high enough to adversely affect the microstructure of the material. The matrix is formed by placing particles, preferably spherical and uniform in size, within a collapsible container that is connected to the body of a prosthetic device, evacuating and sealing the container and subjecting the sealed container to the pressure of an inert gas at controlled temperatures. The controlled application of pressure at a temperature below that which might affect the strength of the material causes the container to collapse and bond the particles together with an interconnected matrix. The isostatic pressure of the inert gas on the container applied with an elevated temperature causes a densification of the particles and a strong bond between them. The collapsed container is then removed and the resulting matrix heat treated in a vacuum to prevent uncontrolled surface oxidation of the material.

The resulting matrix exhibits a strong bond to the substrate metal, a uniform surface and depth and a pore size that can be controlled within predetermined limits from implant to implant to allow for the selective ingrowth of soft or bone tissue. The resulting prosthesis has a high flex strength due to the uniform and integral outer surface of the matrix. Also, since the porous matrix has a controlled depth and pore size, it accommodates tissue ingrowth in such a way as to provide for high strength and durable fixation.

DESCRIPTION OF THE DRAWINGS

A better understanding of the invention can be obtained when the detailed description of an exemplary embodiment set forth below is considered in conjunction with the appended drawings, in which:

FIG. 1 is a perspective view of a hip prosthesis fabricated in accordance with the invention;

FIG. 2 is a perspective view of the hip prosthesis of FIG. 1 before the porous matrix is formed;

FIG. 5 is a graph of percent elongation versus temperature for a titanium alloy (Ti-6Al-4V) material.

DESCRIPTION OF AN EXEMPLARY EMBODIMENT

Figure 3A:
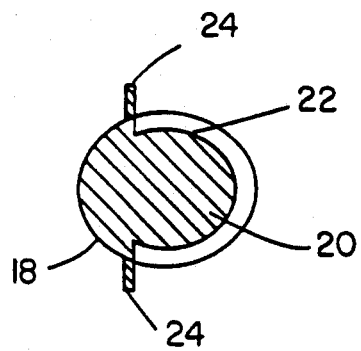
FIGS. 3a-3c are cross-sectional views of the hip prosthesis at various stages of fabrication of the porous matrix, FIG. 3c looking along the section line 3c-3c as shown in FIG. 1.

The porous matrix of the present invention is described in conjunction with a hip prosthesis generally designated by reference numeral 10 as shown in FIG. 1, although such a matrix could be formed on most other types of orthopedic implant devices in accordance with the invention. The prosthesis 10 includes a ball-shaped head 12 formed integral with the remaining portion of the prosthesis 10 or one that can be mounted on a post (not shown) that is formed integral with the remainder of the prosthesis 10. The head 12 is adapted to fit into a prosthetic acetabular cup (not shown) adapted to fit in the pelvis of a patient. The prosthesis 10 also includes a stem portion 14 that is adapted to be inserted in the medullary canal of a femur of a patient prepared to receive the prosthesis 10. As mentioned above, such stems in the past have been fixed in the femur either through the use of bone cement, a friction fit or by providing a porous or other irregular surface on the stem 14 to accommodate tissue ingrowth for holding the stem 14 in place.

The prosthesis of the present invention includes a section 16 that is made up of a porous matrix that is designed to accommodate tissue ingrowth for holding the prosthetic device 10 in place in a patient's femur. The subject invention is directed to such a porous matrix that has a controlled outer surface, depth and pore size that is capable of accommodating tissue ingrowth.

The prosthesis 10 can be formed of any number of biocompatible metals such as stainless steel, cobalt-chromium-molybdenum alloys or titanium alloys. For the purposes of the following descriptions, the prosthesis 10 is formed of a titanium alloy, Ti-6Al-4V, and the porous matrix 16 formed of spherical beads of the same material.

The prosthetic device 10, as shown in FIG. 2, is fabricated initially with a T-shaped cross-section formed between a spine 18 and ridge 20 resulting in a cavity 22 in the normal stem portion 14 of the prosthesis 10. The prosthesis 10 can be fabricated by any of the conventional methods of manufacture, including casting, machining or forging. As will be discussed, a porous matrix is formed within the cavity 22 using the steps illustrated in FIGS. 3a-3c.

Figure 3B:
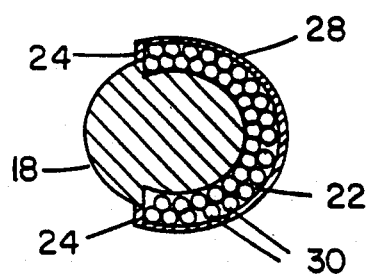

As shown in FIG. 3a, flanges 24 of a collapsible, foil-like metal material are connected to both sides of the spine 18. The flanges 24 can be connected by any suitable means such as welding, soldering or the like. As shown in FIG. 3b, a collapsible, metallic foil-like material is connected to the flanges 24 forming a can or container 28 around the cavity 22. As mentioned above, the prosthesis 10 is formed of a titanium alloy. For such a prosthesis, the flanges 24 and container 28 are preferably formed of a titanium foil lined on the sides facing the cavity 22 with molybdenum. The container is preferably welded to the flanges 24 at their points of connection.

As shown schematically in FIG. 3b, spherical beads or particles 30 of a titanium alloy are charged in the cavity 22 through an opening (not shown) located in the container 28 on both sides of the ridge 20. The opening should be in one of the corners of the container 28 so that the cavity 22 on both sides of the ridge 20 can be completely filled with the beads 30. The spherical beads should be of a uniform spherical shape, about 20-18 mesh, since that size would result in a porous matrix that promotes ingrowth of bone tissue as will be more fully described in the example set forth below. It is within the ability of one with ordinary skill in the art to select an appropriate bead size range to form a porous matrix with the desired pore size.

Figure 3C:
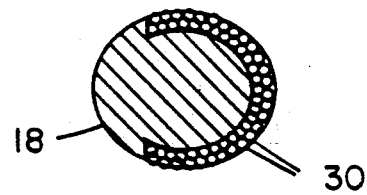

The container 28 is preferably of a size and shape such that the matrix 16 would be two beads deep as shown in FIG. 3c, although other depths could be utilized. A two to three-bead depth results in a matrix 16 that is about 2-2.5 mm in thickness in the finished product.

After the chamber 28 is charged with sufficient beads to completely fill the cavity 22 on both sides of the ridge 20, the cavity 22 is evacuated by suitable vacuum means (not shown) and the openings on each side of the cavity 22 are sealed by suitable means such as welding, soldering or the like. The prosthesis is then subjected to a hot isostatic pressing process (HIP process), which provides for uniform densification of the beads 30 within the container 28 at a temperature that does not adversely effect the microstructure of the substrate.

The HIP process is carried out in an oven that includes an airlock. The prosthesis 10 is prepared as described and placed within the oven, which is then evacuated and charged with an argon atmosphere. The oven is heated to the desired temperature while the atmosphere therein is pressurized to the desired pressure. The HIP process applies an isostatic pressure through an inert gas such as argon. By applying sufficient pressure during the heating step, the beads 30 are fused together and to the adjacent surfaces of the spine 18 and ridge 20 as shown schematically in FIG. 3c, at a temperature below that which transforms the microstructure to a weakened state.

The HIP process can apply pressure up to about 30,000 psi at temperatures from about 27° C. to 1370° C. For a typical titanium alloy prosthesis with titanium alloy beads, a temperature of about 900° C. and a pressure of about 300 psi-500 psi are preferable. The preferred inert gas for use in such an HIP process is argon. The duration of the HIP process can range from about 1 hour to about 4 hours with a preferred time for a titanium alloy matrix of about 2-3 hours depending on configuration and size of the porous matrix to be formed.

After the prosthesis has been subjected to the elevated pressure and temperature sufficient to fuse the particles together and to the remaining portion of the prosthesis 10, the prosthesis is cooled gradually by removing heat from the furnace after pressure has been relieved. The slow furnace cooling controls the formation of stress between the porous matrix and the substrate so that a high-strength durable bond is formed. Also, through the application of heat and pressure in the HIP furnace, the beads 30 are compacted as shown schematically in FIG. 3c so that the beads 30 are flush with the outer edges of the spine 18 for forming a visually pleasing and finished final product. The particle size, pressure and temperature can be regulated so that the outer surface of the beads 30 in the final product will be flush with the outer edges of the spine 18.

After the prosthesis and porous matrix have been cooled to room temperature, the container 28 and flanges 24 are cut away from the prosthesis 10 and the edges machined to provide a smooth outer surface. An outer portion of the flange 26 can be machined to be flush with the outer surface of the beads 30. The porous matrix is left with a uniform surface and depth completely filling the cavity 22.

Figure 4:
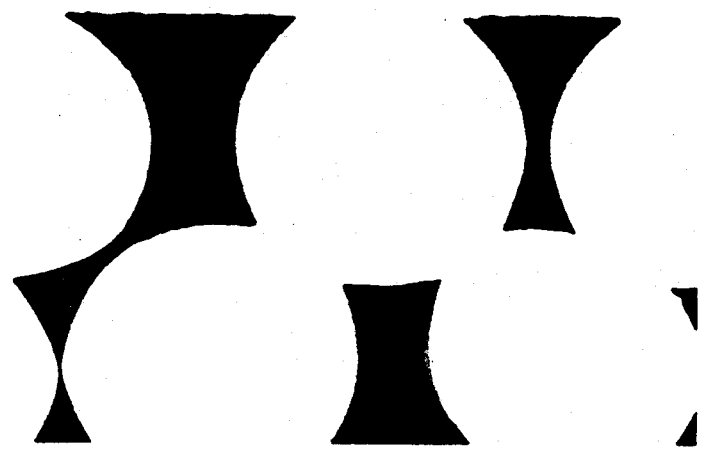
FIG. 4 is a graphic representation of a photomicrograph at 50 times magnification of a porous matrix formed in accordance with the present invention.
Figure 6:
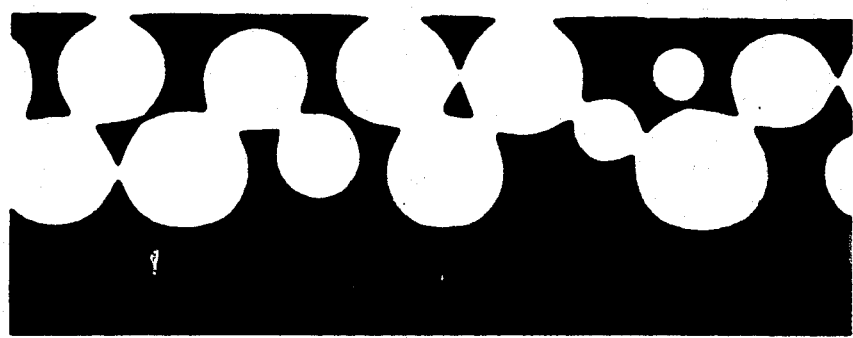
FIG. 6 is a graphic representation of a photomicrograph at 20 times magnification of a porous matrix formed in accordance with the present invention.

A photomicrograph of a substantially uniform porous matrix formed in accordance with the method described above at 50 times magnification is illustrated in FIG. 4. A photomicrograph of a nonuniform matrix formed in accordance with the method described above at 20 times magnification is illustrated in FIG. 6. It has been found that by using the HIP process, a porous coating with consistent pore size is provided because the applied pressures and temperatures avoids severe deformation of the spherical particles 30. A uniform porous matrix (FIG. 4) is desirable though not necessary.

After the container 28 is removed as described, the prosthesis is heat treated in a fan quenched vacuum furnace. The vacuum prevents severe surface oxide formation and is carried out at a temperature below the beta transus for the substrate material so that the microstructure will not be adversely effected. For a titanium alloy such as Ti-6Al-4V, the heat treatment step takes from about 1-3 hours, preferably about 2 hours at a temperature from about 850° C.-950° C., preferably at about 900° C. in a vacuum furnace with an argon fan quenched capability.

After heat treatment, no further thermal treatment or machining of the prosthesis is necessary. The process described above provides a porous matrix that has a uniform surface and infra-structure with no adverse effect on the physical properties of the prosthesis material. The following chart shows physical properties for a Ti-6Al-4V alloy, columns 1-3 showing an untreated material and columns 4-6 for a material subjected to a HIP process:

|  | 1 | 2 | 3 | 4 | 5 | 6 |
|---|---|---|---|---|---|---|
| Tensile Strength (psi) | 140,000 | 138,000 | 139,000 | 139,000 | 139,000 | 140,000 |
| Yield Strength (psi) | 133,000 | 132,000 | 132,000 | 129,000 | 130,000 | 129,000 |
| Elongation (%) | 20 | 21 | 20 | 19 | 19 | 19 |
| Reduction (%) | 55 | 55 | 56 | 51 | 52 | 50 |

The test samples reflected in the chart comprised forged Ti-6Al-4V round bar 1.5" in length and 0.375" in diameter and Ti-6Al-4V powders sieved to a 600 to 850 micron particle size. The powder material was formed around the test specimens in a low carbon steel foil-like material container which was then evacuated. Fusing of the coatings was performed at 900° C. for two hours at 1,450 psi in an argon atmosphere. This was followed by a cooling rate of approximately 10° C. per minute to room temperature. The samples were sectioned transversely using standard metallurgical practices and specimens were examined in both the polished and etched conditions. Etching was performed using a lactic acid solution. Transverse sections were taken at 0.2" intervals in order to perform interfacial shear strength testing. Standard mechanical testing procedures were performed on the substrate material. The chart shows that there is little change in the physical properties of the materials subjected to the HIP process.

FIG. 5 is a graph illustrating the effects of temperature beyond the beta transus of the titanium alloy Ti-6Al-4V. In FIG. 5, the X axis shows temperature at degrees F and the Y axis elongation percentage in pounds per square inch, the graph showing the effects of elevated temperature on a furnace-cooled titanium bar. FIG. 5 illustrates that a temperature such as would be encountered in sintering for the titanium alloy above the beta transus would adversely affect the strength of any prosthesis formed of that material.

EXAMPLES

Example 1

The following procedure was used in preparing a prosthetic device in accordance with the present invention. Ti-6Al-4V spherical powder was first sieved to a −18/+20 mesh size (between 850–1,000 microns). The Ti-6Al-4V prosthetic substrate was prepared to a 600 grit finish and glass beaded. A container consisting of an inner layer of molybdenum foil with an outer layer of Ti-6Al-4V foil was welded to a ridge surrounding the region to be coated. A fill tube was welded to the surface of the can and the device placed within a vacuum. The canned or pocketed region was filled with spherical powder and vibrated to achieve uniform packing of the powder. The prosthetic device with the filled can was placed in a cold HIP furnace. The furnace was filled with argon and the temperature raised to 900° C. A pressure of 500 psi was applied for one hour. The heating and pressure systems were shut off and the system allowed to furnace cool.

The prosthetic device was then removed and the container machined off. The stem was placed in a solution of 65% $HNO_3$ and 35% water under ultrasonic vibration for a period of two hours at 50° C. The stem was heat treated by placing in a vacuum furnace where a vacuum is pulled on the system and the temperature raised to 900° C. The prosthetic device was allowed to soak for a period of one hour before being quenched with an inert gas to room temperature. A material prepared in accordance with the above procedure exhibited an interfacial shear strength of 31,074 psi ±3,126, a tensile strength of 137,000 psi, a yield strength of 120,500 psi, elongation to failure of 20%, reduction of area 54%, hardness (Rc) of 30, a percent porosity of 25.8 and a pore size in microns of 256.5.

It should be understood that the foregoing description and drawings of the invention are not intended to be limiting, but are only exemplary of the inventive features that are defined in the claims and that improvements and modifications could be made to the described prosthetic device and method, all such improvements and modifications falling within the scope of the appended claims.

We claim:

1. A method of forming a porous matrix on a portion of the outer surface of a prosthetic device, comprising the steps of:
   (a) providing a prosthetic device having an outer surface portion on which a porous matrix is to be formed;
   (b) attaching an enclosure around said outer surface portion that conforms to the shape of the prosthetic device outer surface and spaced therefrom, said enclosure having a smooth inner surface for engaging metallic particles contained within the enclosure, and wherein the enclosure is formed of a collapsible material capable of withstanding elevated temperature;
   (c) charging the space between the enclosure inner surface portion and the outer surface of the prosthetic device with metallic particles;
   (d) evacuating substantially all air from said enclosure;
   (e) subjecting the outer surface of said enclosure to an elevated pressure in an atmosphere of inert gas at an elevated temperature;
   (f) wherein in step "e" said pressure and temperature are sufficient to fuse the particles together and to said portion of the prosthetic device so that the inner surface of the collapsed enclosure deforms at least some of the metallic particles to define a smooth but porous outer surface of the prosthetic collapsed metallic particles at a temperature below that which would transform the microstructure of the metallic substrate to a weakened state;
   (g) cooling said prosthetic device;
   (h) removing said enclosure to expose said particles; and
   (i) wherein in step "h" the prosthesis outer surface remains smooth but porous after removal of the enclosure.

2. The method of claim 1, wherein said portion includes a cavity formed on the outer surface of the prosthetic device and conforming to the shape of the prosthetic device on multiple sides thereof.

3. The method of claim 1, wherein said prosthetic device and metallic particles are formed of a titanium alloy, Ti-6Al-4V.

4. The method of claim 1, wherein said enclosure is formed of a titanium alloy foil lined with molybdenum on the side in contact with the metallic particles.

5. The method of claim 1, wherein the metallic particles are spherical in shape and in step "f" the particles are flattened at the surface of the prosthesis to define the smooth outer surface.

6. The method of claim 1, wherein said particles are of a mesh from 20 to 18.

7. The method of claim 3, wherein step (e) is performed at a temperature below the beta transition temperature of the particle material.

8. The method of claim 7, wherein step (e) is performed at a temperature of about 900° C.

9. The method of claim 1, wherein step (e) is performed in a hot isostatic press.

10. The method of claim 1, wherein said inert gas is argon.

11. The method of claim 9, wherein said hot isostatic process is performed at a pressure between about 300-500 psi.

12. The method of claim 9, wherein the step (e) is maintained for about 1-4 hours.

13. The method of claim 1, and further including the step of heat treating the porous matrix in a fan quenched vacuum furnace to prevent surface oxidation of the particles.

14. The method of claim 1, wherein said prosthetic device is a hip prosthesis with a femoral stem portion having medial and lateral side portions, and said porous matrix is applied to the proximal region of said femoral stem and on multiple sides thereof including at least medial and lateral side portions thereof.

15. A method of forming a porous matrix on a portion of outer surface of a hip prosthesis having a lower elongated distal stem, a proximate portion with anterior and posterior sides, and a neck region, comprising the steps of:
   (a) providing a hip prosthesis having an outer surface portion on which a porous matrix is to be formed and including a lower stem proximate portion and a neck region;
   (b) attaching a metallic enclosure around said outer surface portion at the mid portion thereof, terminating below the neck and adjacent the stem, the enclosure conforming generally to the shape of the his prosthesis proximate portion and extending over at least the anterior and posterior sides thereof and spaced therefrom, said enclosure having a smooth inner surface portion and being formed of a collapsible material capable of withstanding the temperature of step (e);
   (c) charging the space between the enclosure inner surface portion and the outer surface of the prosthetic device with metallic particles;
   (d) evacuating substantially all air from said enclosure;
   (e) subjecting the outer surface of said enclosure to an elevated pressure in an atmosphere of inert gas at an elevated temperature;
   (f) wherein the step "e" said pressure and temperature are sufficient to fuse the particles together and to said portion of the hip prosthesis so that the inner surface of the collapsed enclosure deforms at least some of the metallic particles to define a smooth but porous outer surface of the prosthetic collapsed metallic particles at a temperature below that which would transform the microstructure of the metallic substrate to a weakened state;
   (g) cooling said hip prosthesis device;
   (h) removing said enclosure to expose said particles; and
   (i) wherein in step "f" a plurality of the particles are flattened at the outer surface to define the smooth surface, the smooth outer surface remaining smooth but porous after removal of the enclosure in step "h".

* * * * *